United States Patent [19]

Haire

[11] 4,123,546

[45] Oct. 31, 1978

[54] ANTIDEPRESSANT COMPOUNDS

[75] Inventor: Michael J. Haire, Newark, Del.

[73] Assignee: E. I. Du Pont de Nemours and Company, Wilmington, Del.

[21] Appl. No.: 812,405

[22] Filed: Jul. 1, 1977

[51] Int. Cl.$^2$ .................... A61K 31/40; C07D 471/18
[52] U.S. Cl. ............................ 424/274; 260/326.5 B; 260/288 CF; 260/239 E
[58] Field of Search ................. 260/326.5 B; 424/274

[56] References Cited

U.S. PATENT DOCUMENTS 4,009,273   2/1977   Nedelec et al. ............... 260/288 CF Primary Examiner—Jose Tovar

[57] ABSTRACT

Antidepressant compounds such as 2-[(4b,4c-dihydro-8bH-azirino[2,1,3-cd]dibenzo[a,f]pyrrolizin-8b-yl)oxy]ethyl-N,N-dimethylamine useful for alleviating depression in mammals.

18 Claims, No Drawings

ANTIDEPRESSANT COMPOUNDS

BACKGROUND OF THE INVENTION

This invention relates to compounds which are useful in alleviating depression in mammals.

The following publications disclose 5,10-iminodibenzocycloheptenes:

J. W. Lown and K. Matsumoto, *J. Org. Chem.*, 36, 1405 (1971)
French Pat. No. 2,170,862
French Pat. No. 2,174,771
U.S. Pat. No. 4,009,273

The compounds have the structure

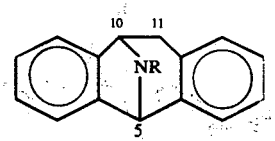

wherein the nitrogen can have H, lower alkyl, hydroxyalkyl, aminoalkyl, carbamyl or carbonyl containing groups, and the 11-position can have hydrogen or oxygen. The references show no substituent on the 5-position except for phenyl shown by Lown et al. Suitable utility, if disclosed for these compounds, is as an anticonvulsant, antidepressant, sedative or stimulant.

Netherlands Pat. No. 147,935 discloses compounds as antidepressants of the formula:

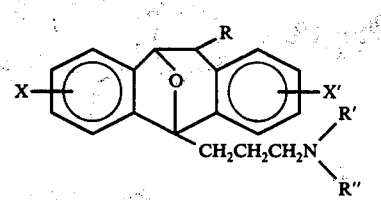

where X, X', R, R' and R" represent various substituents.

Mental illness encompasses both psychoses and neuroses. Symptoms requiring treatment include depression, anxiety, agitation, and hallucinations. Among the drugs used particularly for treatment of both reactive and endogenous depressions are monoamine oxidase (MAO) inhibitors, such as iproniazide, tranylcypromine, nialamide, phenelzinc, and pargyline, and the non-MAO-inhibiting tricyclic aromatic dibenzazepines, such as imipramine, and dibenzocycloheptenes such as amitriptyline.

All of these drugs have adverse side effects that limit their usefulness. MAO inhibitors may benefit milder forms of depression, but the risk of serious toxic effects is a strong argument against their use. They may cause liver damage and acute hypertension, especially if given in conjunction with cheese, bananas, or other amine-containing foods. The MAO inhibitors may also cause tremors, insomnia, hyperhydrosis, agitation, hypermanic behavior, confusion, hallucinations, convulsions and orthostatic hypotension. They frequently cause dizziness, vertigo, headache, inhibition of ejaculation, difficulty in urination, weakness, fatigue, dry mouth, constipation and blurred vision.

Imipramine may cause blurred vision, dryness of mouth, constipation, urinary retention, orthostatic hypotension, respiration depression, myocardial infraction, and congestive heart failure. Similar difficulties are experienced with amitriptyline.

There is a continuing need for psychotherapeutic agents that have fewer side effects than the drugs in use today; use for psychotherapeutic agents that have different modes of action than presently used agents, since none of these is completely effective.

The present invention results from efforts to develop new, safe, and effective psychotherapeutic compounds with minimal side effects.

SUMMARY OF THE INVENTION

According to this invention, there is provided novel compounds of formula I, compounds of formula II, their pharmaceutically suitable acid addition salts, processes for their manufacture, compositions containing them, and method of using them to alleviate depression in mammals.

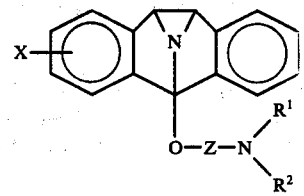

where
X is H, F, Cl, Br, $C_{1-4}$ alkyl, $C_{1-4}$ alkoxy, $CF_3$ or $C_{1-4}$ alkyl sulfonyl,
Z is $C_2$–$C_3$ alkylene; and
$R^1$ and $R^2$, independently, are H or $C_{1-4}$ alkyl.

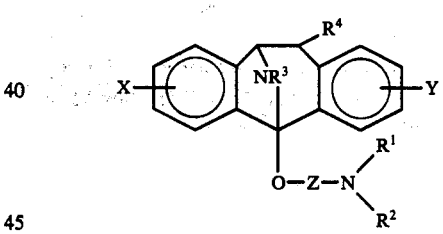

where
X and Y, independently, are H, F, Cl, Br, $C_{1-4}$ alkyl, $C_{1-4}$ alkoxy, $CF_3$ or $C_{1-4}$ alkyl sulfonyl with the proviso that one of X and Y is H;
Z is $C_2$–$C_3$ alkylene
$R^1$ and $R^2$, independently, are H or $C_{1-4}$ alkyl,
$R^3$ is H or $C_{1-4}$ alkyl, and
$R^4$ is H or halogen.

Also provided are compounds of formula III which are intermediates in preparation of compounds of formula I and II.

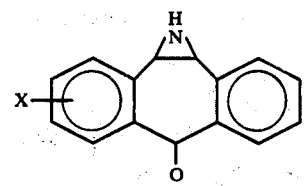

where X is as previously defined.

DETAILED DESCRIPTION OF THE INVENTION

Preferred Compounds

Compounds preferred because of their high degree of activity are those in formula I in which $R^1$ and $R^2$ independently are H or $CH_3$.

More preferred are those in which X is H, Z is ethylene ($CH_2CH_2$), and $R^1$ and $R^2$ independently are H or $CH_3$.

The compound most preferred is that in which X is H, Z is ethylene, and $R^1$ and $R^2$ are H.

Compounds of formula II also have the preferred definitions as the constituents of formula I but in addition Y is H, and $R_4$ is H or Cl.

Pharmaceutical Salts

Pharmaceutically suitable acid addition salts of these compounds of formula I and formula II include those made with physiologically acceptable acids that are known in the art; such salts include hydrochloride, sulfate, nitrate, phosphate, citrate, tartrate, maleate and the like.

Nomenclature

The compounds of formula I can be named as azadibenzosemibullvalenes or in conformity with chemical nomenclature rules. A compound of formula I with the structure

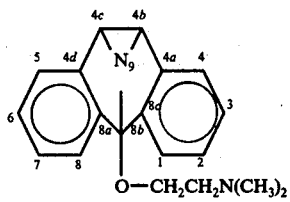

can be named 2-[(4b,4c-dihydro-8bH-azirino[2,1,3-cd]-dibenzo[a,f]pyrrolizin-8b-yl)oxy]-ethyl-N,N-dimethylamine. A compound of formula II such as

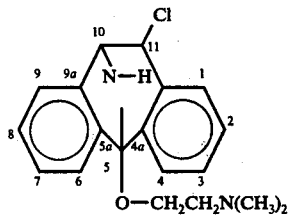

can be named 10,11-dihydro-5,10-imino-5-[2-(N,N-dimethylamino)-ethoxy]-11-chloro-5H-dibenzo[a,d]cycloheptene while the intermediates of the type of formula III can be named as a 10,11-dihydro-10,11-azacyclopropa-5H-dibenzo[a,d]cyclohepten-5-one.

Synthesis

Compounds of this invention are prepared as shown in the following general reaction scheme.

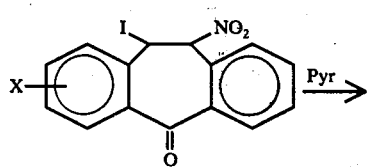

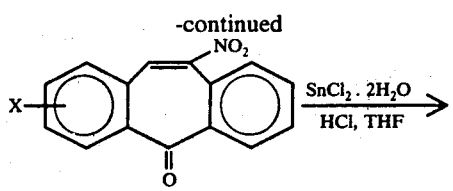

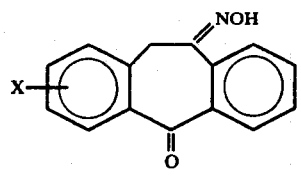

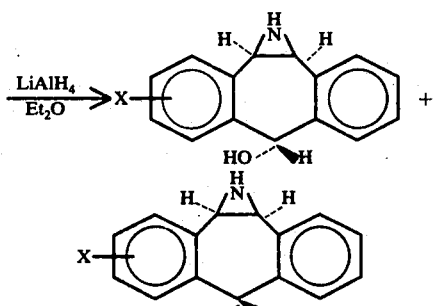

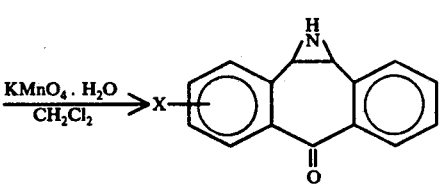

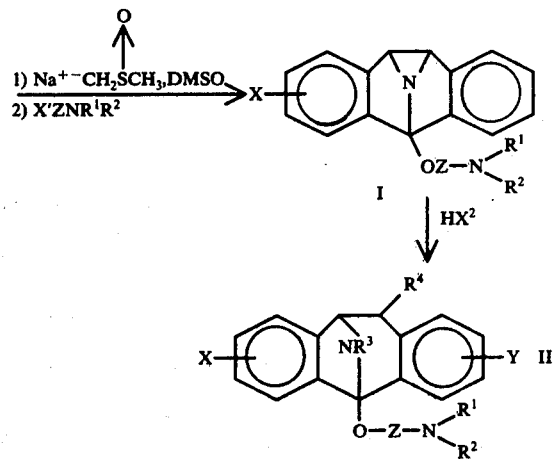

in which $R^1$, $R^2$, $R^3$, X, Y and Z are as previously defined, $X^1$ and $X^2$ are halogen, e.g. chlorine, and $R^4$ is the same as $X^2$.

Although it is understood that the same reaction procedure applies with X as previously defined, X (and also Y) where applicable is hydrogen in the following discussion.

Initially 10-iodo-11-nitro-5H-dibenzo[a,d]cyclohepten-5-one is contacted with pyridine to form 10-nitro-5H-dibenzo[a,d]cyclohepten-5-one. This compound is reduced to 10,11-dihydro-10-hydroximino-5H-dibenzo[a,d]cyclohepten-5-one employing a solution of stannous chloride in concentrated hydrochloric acid and tetrahydrofuran generally at 0°–50° C. for 2–16 hours.

A further reduction e.g. using lithium aluminum hydride in ether or tetrahydrofuran generally at 0°–65° C. for 1–3 hours forms syn- or anti-10,11-dihydro-10,11-azacyclopropa-5H-dibenzo[a,d]-cyclohepten-1-ol.

Thereafter either or both of these compounds are oxidized under suitable conditions to form an intermediate compound, 10,11-dihydro-10,11-azacyclopropa-5H-dibenzo[a,d]-cyclohepten-5-one. This oxidation employs a suitable oxidation reagent such as 2,3-dichloro-5,6-dicyanoquinone (DDQ) with dioxane as a solvent. Alternatively a chromium trioxide/pyridine complex in methylene chloride can be employed for the oxidation, generally at 0°–25° C. Preferred oxidation is obtained when a permanganate, e.g. $KMnO_4$, is a saturated aqueous salt solution, e.g. of $MgSO_4$, and an inert solvent, including halogenated hydrocarbons such as methylene chloride, is used.

Formation of the azasemibullvalene structure

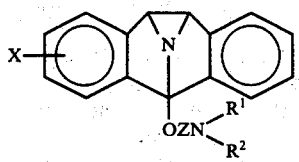

I with $R^1$, $R^2$, N and Z previously defined initially involves contacting the oxidized intermediate with dimsyl alkali metal salt, generally at 15°–65° C. This salt can be preformed e.g., with sodium hydride and dimethylsulfoxide. Thereafter the product is contacted with an appropriate alkylating agent of the formula $R^1R^2NZX^1$ with $X^1$ defining a halogen such as chlorine, generally at 15°–65° C.

Conversion of the structure of formula I to a pharmaceutically suitable acid addition salt can be in accordance with conventional techniques since the compounds have amino nitrogen.

Compounds of formula II are prepared from those of Formula I by reaction with a hydrogen halide, especially HCl or HBr. If desired, the halogen in the 11-position can be replaced by other groups, e.g., hydrogen by reduction. Also conversion of the structure of Formula II to a pharmaceutically suitable acid addition salt can be in accordance with conventional techniques.

The starting materials of 10-iodo-11-nitrodibenzocycloheptenes are disclosed in U.S. Pat. No. 3,883,593.

In the following illustrative examples, all parts are by weight and temperature are degrees centigrade unless stated to be otherwise.

EXAMPLE 1

A.
10,11-Dihydro-10-hydroximino-5H-dibenzo[a,d]cyclohepten-5-one

To a solution of 40 g (160 mmol) of 10-nitro-5H-dibenzo-[a,d]cyclohepten-5-one (obtained by the process of Example 1 of U.S. Pat. No. 3,883,593) in 1200 ml of tetrahydrofuran and 70 ml of concentrated hydrochloric acid at 0° was added slowly with stirring a solution of 111 g (585 mmol) of stannous chloride in 420 ml of tetrahydrofuran and 165 ml of concentrated hydrochloric acid. The mixture was stirred at 0° for 3 hrs, followed by 2 hrs at room temperature. The yellow solution was then poured into 3000 ml of methylene chloride and washed with water, 5% aqueous hydrochloric acid, water, saturated aqueous sodium carbonate, and water. The organic layer was dried, filtered, and concentrated in vacuo to give a yellow solid which was recrystallized from absolute ethanol to give 28.0 g (118 mmol, 74%) of 10,11-dihydro-10-hydroximino-5H-dibenzo[a,d]cyclohepten-5-one as light yellow crystals, m.p. 186°–186.5° C.

Anal. Calcd. for $C_{15}H_{11}NO_2$: C, 75.94; H, 4.67; N, 5.90. Found: C, 76.15; H, 4.77; N, 5.90. MS Calcd for $C_{15}H_{11}NO_2$: 237.0789. Found 237.0788.

B. Syn- and Anti-10,11-dihydro-10,11-azacyclopropa-5H-dibenzo[a,d]cyclohepten-5-ol The technique of Cioranescu et al., *Revue Roumaine de Chimie*, 16 (no. 10), 1555–1566 (1971) was employed. To a suspension of 28 g (0.747 mol) of lithium aluminum hydride in 1 l. of dry ether under nitrogen was added 35 g (0.147 mol) of 10,11-dihydro-10-hydroxyimino-5H-dibenzo[a,d]cyclohepten-5-one in 2 l. of ether at room temperature over 30 min. The mixture was stirred and refluxed for 3 hrs, cooled with an ice bath, and the excess lithium aluminum hydride was destroyed by carefully adding 1000 ml of ice water. The mixture was then extracted with ether (6×), and the ether extracts were dried, filtered, and concentrated in vacuo to give a yellow solid which was washed with hot ether (3 × 30 ml) and vacuum dried to giving 21.64 g of off-white solid. The solid was washed twice with 20 ml of chloroform, filtered, and vacuum dried giving 12.74 g (57.1 mmol, 39%) of anti-10,11-dihydro-10,11-azacyclopropa-5H-dibenzo[a,d]-cyclohepten-5-ol as an off-white solid, m.p. 186°–188° C. Concentration of the chloroform filtrate yielded 10.13 g (45.4 mmol, 31%) of syn-10,11-dihydro-10,11-azacyclopropa-5H-dibenzo[a,d]cyclohepten-5-ol as an off-white solid, m.p. 163°–165°.

The spectral data for the syn product were: nmr (CDCl₃) τ 2.30–2.90 (m, 8 H, arom), 3.72 (br d, 1 H, J = 11 Hz,

6.25–6.55 (br s, 2 H, benzylic), and 7.18–8.03 (br m, 2 H, —NH and —O—H). ir (CHCl₃) 2.98, 3.30, 6.70, 6.90, 7.10, 7.17, 7.60, 7.68, 8.00, 8.45, 8.82, 9.02, 9.51, 9.90, 10.56, 11.02, 11.27, 12.20, 12.51, and 14.22μ.

Anal. Calcd for $C_{15}H_{13}NO$: C, 80.69; H, 5.87; N, 6.27. Found: C, 80.70; H, 6.08; N, 6.27. MS Calcd. for $C_{15}H_{13}NO$: 223.0997. Found: 223.0989.

The spectral data for the anti product were: nmr (DMSO-d₆) τ 2.20–3.10 (m, 8 H, arom), 4.40 (d, 1 H, J = 5 Hz,

6.32–6.90 (br m, 3 H, benzylic), and 7.17–7.82 (br m, 1 H, —NH). ir (nujol) 3.07, 3.42, 6.72, 6.83, 7.27, 7.54, 7.67, 7.97, 8.17, 8.39, 8.47, 8.92, 9.57, 10.21, 10.55, 11.16, 11.67, 12.48, 12.83, 12.95, 13.27, 13.62, and 14.08μ.

Anal. Calcd. for $C_{15}H_{13}NO$: C, 80.69; H, 5.87; N, 6.27. Found: C, 80.55; H, 6.07; N, 6.36. MS Molecular ion at m/e 223.

C.
10,11-Dihydro-10,11-azacyclopropa-5H-dibenzo[a,d]-cyclohepten-5-one

(1) From Syn-10,11-dihydro-10,11-azacyclopropa-5H-dibenzo[a,d]cyclohepten-5-ol To a stirred solution of 9.49 g (120 mmol) of pyridine in 150 ml of methylene chloride under nitrogen at room temperature was added 6 g (60 mmol) of chromium trioxide. A solution of 2.23 g (10 mmol) of syn-10,11-dihydro-10,11-azacyclopropa-5H-dibenzo[a,d]cyclohepten-5-ol in 15 ml of methylene chloride was added in one portion. After stirring for 20 min, the solution was decanted from a tarry residue, filtered, and washed with saturated aqueous sodium bicarbonate and brine, then dried, filtered, and concentrated in vacuo to give 1.16 g of dark oil which was chromatographed on two 20 cm × 20 cm × 2 mm plates of silica gel.

After one elution with chloroform, the fourth band from the top was collected giving 830 mg of oil. The oil was triturated with ethanol, filtered, washed with ethanol, and vacuum dried giving 180 mg (0.81 mmol, 8%) of 10,11-dihydro-10,11-azacyclopropa-5H-dibenzo[a,d]cyclohepten-5-one as a white solid, m.p. 189°–191° (dec.).

The above ketone was also prepared by oxidation with potassium permanganate either (a) under substantially anhydrous conditions in the presence of dicyclohexyl-18-crown-6 or (b) in an aqueous salt media. The latter procedure was as follows: To 8.1 g of $KMnO_4$ stirred in 100 ml of saturated aqueous $MgSO_4$ was added 10 g of syn-10,11-dihydro-10,11-azacyclopropa-5H-dibenzo[a,d]cyclohepten-5-ol. The mixture was stirred 5 minutes and 200 ml of $CH_2Cl_2$ added, stirred for 16 hrs, diluted with 300 ml of $CH_2Cl_2$, washed with saturated aqueous $Na_2SO_3$, then washed with water, dried, decolorized by charcoal, filtered and the filtrate concentrated under vacuum to give a yellow solid. The latter was crystallized from ethanol to give about 1.5 g each of starting alcohol and the ketone.

(2) From Anti-10,11-dihydro-10,11-azacyclopropa-5H-dibenzo[a,d]cyclohepten-5-ol To a stirred solution of 124.72 g (1.58 mol) of pyridine in 1500 ml of methylene chloride under nitrogen at room temperature was added 78.84 g (0.788 mol) of chromium trioxide. The mixture became deep red, and was allowed to stir for 15 minutes whereupon a suspension of 29.32 g (0.131 mol) of anti-10,11-dihydro-10,11-azacyclopropa-5H-dibenzo[a,d]cyclohepten-5-ol in 650 ml of methylene chloride was added in one portion. After stirring for 20 minutes, the solution was decanted from a black tarry deposit, filtered, washed with saturated aqueous sodium bicarbonate and brine, dried, filtered, and concentrated in vacuo to give a brown solid which was recrystallized from 100 ml of ethanol to give 11.97 g (0.054 mol, 47%) of 10,11-dihydro-10,11-azacyclopropa-5H-dibenzo[a,d]cyclohepten-5-one, m.p. 189°–190° (dec.).

Anal. Calcd (from a sample prepared by a similar experiment) for $C_{15}H_{11}NO$: C, 81.43; H, 5.01; N, 6.33. Found: C, 81.52; H, 5.09; N, 6.41. MS Calcd. for $C_{15}H_{11}NO$: 221.0840. Found: 221.0859.

The use of potassium permanganate was found to be a preferred process for oxidizing the anti-alcohol. By following the general procedure used in the preceding section for oxidizing the syn-isomer, the ketone was obtained in a 59% yield with the crown compound and a 71% yield with aqueous magnesium sulfate. The spectral data for the ketone follows: nmr ($CDCl_3$) τ 2.29–2.90 (m, 8 H arom), 6.34 (br d, 2 H, J = 9 Hz, benzylic), and 6.69–7.37 (br m, 1 H, —NH—). ir ($CHCl_3$) 3.00, 3.30, 5.98 (s), 6.24, 6.70, 6.89, 7.19, 7.75, 8.08, 8.41, 8.68, 8.80, 9.14, 9.60, 10.50, 10.73, 11.00, 11.70, 12.20, 12.50, and 14.04μ.

EXAMPLE 2

2-[(4b,4c-Dihydro-8bH-azirino[2,1,3-cd]dibenzo[a,f]pyrrolizin-8b-yl)oxy]ethyl-N,N-dimethylamine Dimsyl sodium was prepared by heating and stirring under $N_2$ a mixture of 360 mg (14.0 mmol) of sodium hydride and 30 ml. of dimethyl sulfoxide to 75° and then allowing it to cool slowly to 55°. To the dimsyl sodium solution at 55° was added a solution of 1.54 g (6.97 mmol) of 10,11-dihydro-10,11-azacyclopropa-5H-dibenzo[a,d]cyclohepten-5-one in 15 ml. of dimethyl sulfoxide dropwise. After stirring for 5 minutes, 1.10 g (7.64 mmol) of 2-(N,N-dimethylamino)ethyl chloride hydrochloride was added in one portion followed by 1.14 g (7.60 mmol) of sodium iodide. The mixture was stirred at 60° for 4 hrs, cooled to room temperature, poured into 150 ml of brine, and extracted with methylene chloride. The organic extracts were washed with brine, dried, filtered and concentrated in vacuo to give 2.14 g of dark oil. The oil was chromatographed on silica gel plates (chloroform elution) giving 1.56 g (5.34 mmol, 77%) of 2-[(4b, 4c-dihydro-8bH-azirino-[2,1,3-cd]dibenzo[a,f]pyrrolizin-8b-yl)oxy]ethyl-N,N-dimethylamine.

nmr ($CDCl_3$) τ 2.50–3.00 (m, 8H, arom), 5.84 (s, 2H, benzylic), 6.05 (t, 2H, J = 6Hz, —$OCH_2$—), 7.20 (t, 2H, J = 6Hz, —N—$CH_2$—), and 7.60 (s, 6H, —$N(CH_3)_2$).

ir ($CHCl_3$) 3.37, 3.57, 6.85, 7.91, 8.07, 8.82, 9.16, 9.51, 9.84, 10.98 and 11.39μ.

Anal. MS Calcd. for $C_{19}H_{20}N_2O$: 292.1575. Found: 292.1565.

EXAMPLE 3

2-[4b,4c-Dihydro-8bH-azirino[2,1,3-cd]dibenzo[a,f]pyrrolizin-8b-yl)oxy]ethyl-N,N-dimethylamine Maleate To a hot solution of 200 mg. (1.72 mmol) of maleic acid in 25 ml. of ethyl acetate was added a hot solution of 500 mg. (1.71 mmol) of 2-[(4b, 4c-dihydro-8bH-azirino[2,1,3-cd]dibenzo-[a,f]pyrrolizin-8b-yl)oxy]ethyl-N,N-dimethylamine in 5 ml. of ethyl acetate. The mixture was cooled to room temperature, the solvent was removed in vacuo, and the residue was stirred with 75 ml. of ether under $N_2$ for 4 days. The suspension was filtered under a nitrogen atmosphere giving 590 mg. (1.45 mmol), 85%) of the maleate salt of 2-[(4b, 4c-dihydro-8bH-azirino-[2,1,3-cd]dibenzo[a,f]pyrrolizin-8b-yl)oxy]ethyl-N,N-dimethylamine as a cream colored solid, m.p. 78° (foaming).

EXAMPLE 4

2-[(4b,4c-Dihydro-8bH-azirino[2,1,3-cd]dibenzo[a,f]-pyrrolizin-8-b-yl)oxyethylamine When the general procedure of Example 2 was repeated except that β-chloroethylamine was used as the alkylating agent, the title compound was obtained in 5% yield. It has nmr of (CDCl₃) τ2.45–3.00 (m, 8H, arom), 5.85 (s, 2H, benzylic), 5.90–6.30 (m, 2H, —O—CH₂—), 6.80–7.80 (m, 4H, —CH₂—NH₂).

This compound was also obtained by reaction of dimsyl sodium with 10,11-dihydro-10,11-azacyclopropa-5H-dibenzo-[a,d]cyclohepten-5-one with chloroacetonitrile to give [(4b, 4c-dihydro-8bH-azirino[2,1,3-cd]dibenzo[a,f]pyrrolizin-8b-yl)oxy]acetonitrile, m.p. 123°–124° C.

Anal. Calcd. for C₁₇H₁₂N₂O: C, 78.44; H, 4.65; N, 10.76. Found: C, 78.34; H, 4.69; N, 10.59.

This compound was treated with a 2 molar amount of lithium aluminum hydride in ether to give the corresponding oxyethylamine in about an 18% yield.

Anal. MS Calcd. for C₁₇H₁₆N₂O: 264.1254; Found: 264.1258.

The tartrate of this compound was formed by mixing equimolar quantities of it with tartaric acid in isopropanol. The salt melted at 100° with foaming and contained an equivalent of isopropanol.

The maleate was prepared by reaction in ethyl acetate, the latter being removed by vacuum. The salt melted at 100° with foaming.

EXAMPLE 5

3-[(4b,4c-Dihydro-8bH-azirino[2,1,3-cd]dibenzo[a,f]-pyrrolizin-8b-yl)oxy]propyl-N,N-dimethylamine Repetition of the process of Example 2 with γ-chloro-N,N-dimethylpropylamine hydrochloride give the above compound in 54% yield.

nmr (CDCl₃) τ 2.50–3.00 (m, 8H, arom), 5.86 (s, 2H, benzylic), 6.19 (t, 2H, J = 6Hz, —O—CH₂—), 7.20–8.28 (m, 4H, —CH₂—CH₂—N), and 7.78 (s, 6H, —N(CH₃)₂); ir (CHCl₃) 3.40, 3.55, 6.83, 7.90, 8.07, 8.41, 8.82, 9.19, 9.50, 11.00, and 13.85μ.

Anal. MS Calcd. for C₂₀H₂₂N₂O: 306.1731. Found: 306,1737.

As demonstrated in U.S. Pat. No. 3,883,593, 10-nitro-5H-dibenzo[a,d]cycloheptene-5-one compounds having substituents on aromatic rings are readily available For use in this invention those having up to one nuclear substituent of F, Cl, Br, CF₃, alkyl, alkoxy, or alkyl sulfonyl wherein the alkyl or alkoxy is of 1–4 carbons are readily available. The nitro group on these compounds can be readily reduced to the oxime (hydroxyimino) as shown by Example 1A and the nuclear carbonyl reduced, e.g., by lithium aluminum hydride to the hydroxy while the hydroxyimino group in converted to the azacyclopropa group at the 10,11-positions as shown by Example 1B. Oxidation of the latter compound with chromium trioxide, potassium permanganate or other conventional oxidizing agents such as the substituted quinones give the new 5 keto compounds as described in Example 1. These have the formula

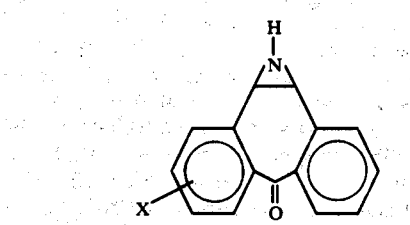

where X is H, halogen, lower alkyl or alkoxy, CF₃, or lower alkylsulfonyl. The starting materials for the above with these substituents are described in U.S. Pat. No. 3,883,593 and include

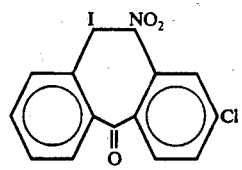

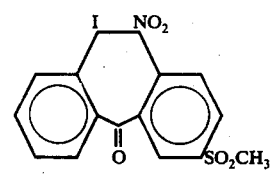

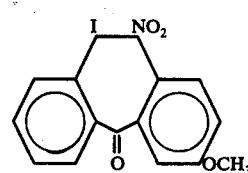

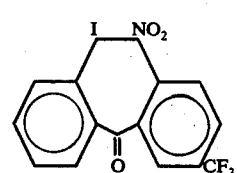

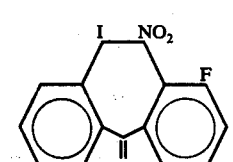

The compounds of formula III give the new compounds of formula I on treatment with an alkali metal (as an organometallic salt) and the alkylating agent R¹R²N(CH₂)₂,₃X¹ where X¹ is halogen, esp. Cl or Br. Alkylating agents include ClCH₂CH₂N(C₄H₉)₂, Br(CH₂CH₂CH₂N(C₃H₃)(CH₃) and ClCH₂CH₂CH₂NH(C₂H₅).

New compounds available as described and useful as antidepressants or for the preparation of other compounds include the following:

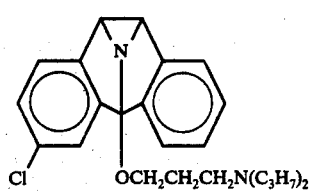

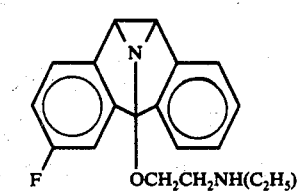

-continued

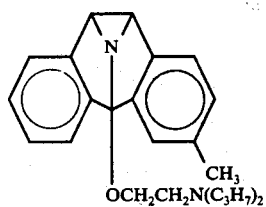
OCH₂CH₂N(C₃H₇)₂

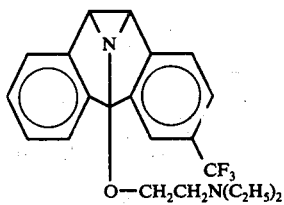
O—CH₂CH₂N(C₂H₅)₂ / CF₃

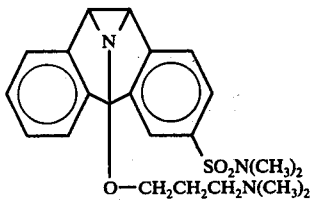
O—CH₂CH₂CH₂N(CH₃)₂ / SO₂N(CH₃)₂

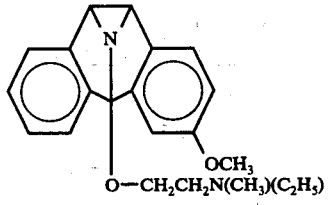
O—CH₂CH₂N(CH₃)(C₂H₅) / OCH₃

As previously discussed, compounds of formula II are prepared from those of formula I by reaction with a hydrogen halide, especially HCl or HBr. If desired, the halogen in the 11-position can be replaced by other groups, e.g., hydrogen by reduction. The following examples illustrate specific compounds available by such procedures:

EXAMPLE 6

10,11-Dihydro-5,10-imino-5-(2-aminoethoxy)-11-chloro-5H-dibenzo[a,d]cycloheptene A mixture of 400 mg (1.52 mmol) of 2-[(4b, 4c-dihydro-8bH-azirino[2,1,3-cd]dibenzo[a,f]pyrrolizin-8b-yl)oxy]-ethylamine and 125 ml of 3N HCl in ethanol was warmed to effect solution, stirred for 3 hrs at room temperature, and concentrated in vacuo. The residue was treated with 200 ml of saturated aq. sodium carbonate and extracted with methylene chloride. The organic extracts were washed with water, dried, filtered, and concentrated in vacuo to give 350 mg (1.16 mmol, 77%) of 10,11-dihydro-5,10-imino-5-(2-aminoethoxy)-11-chloro-5H-dibenzo[a,d]-cycloheptene as a clear light brown oil The spectral data were: nmr (CDCl₃): τ 2.35–3.05 (m, 8H arom), 4.57 (d, 1H, J = 5Hz, PhCHCl—), 5.26 (d, 1H, J = 5Hz, PhCHNH—)6.0–7.28(m, 7H, —NH— and —O—CH₂CH₂NH₂); ir (CHCl₃) 3.09, 3.39, 6.28, 6.78, 6.85, 7.19, 7.45, 8.10, 8.78, 9.16, 9.85, 11.00, 11.40, 11.90, 12.28, and 14.50μ.

EXAMPLE 7

10,11-Dihydro-5,10-imino-5-(2-aminoethoxy)-5H-dibenzo-[a,d]cycloheptene

The compound of Example 6 was dissolved in ether and added slowly to lithium aluminum hydride in ether and refluxed for 5 hrs and allowed to stand for 15 hrs. After treatment with water, dilute sodium hydroxide and water followed by chromatography on silica gel with ethanol, a 5% yield of the above-named compound was obtained, mp 141°–142°.

Anal. MS Calcd for C₁₇H₁₈N₂O: 266.1418. Found: 266.1402.

EXAMPLE 8

10,11-Dihydro-5,10-imino-5-[2-(N,N-dimethylamino)-ethoxy]-11-chloro-5H-dibenzo[a,d]cycloheptene The compound prepared as in Example 2 was reacted with alcoholic HCl as in Example 6 to give the subject compound in a 69% yield. The compound had the following spectral data: nmr (CDCl₃): τ 2.30–2.95 (m, 8H, arom), 4.50 (d, 1H, J = 5.5Hz,

PhCHNH—), 5.20 (d, 1H, J = 5.5Hz,

PhCHCl), 6.05 (t, 2H, J = 5.5Hz, —OCH₂—), 7.26 (t, 2H, J = 5.5Hz, —CH₂—N(CH₃)₂), and 7.61 (s, 6H, —N(CH₃)₂; ir (CHCl₃): 3.36, 6.84, 7.21, 7.46, 7.76, 7.91, 8.12, 8.42, 8.78, 9.52, 10.52, 11.02, 11.87, 12.27, 13.92, and 14.52μ.

EXAMPLE 9

10,11-Dihydro-5,10-imino-5-[2-(N,N-dimethylamino)-ethoxy]-5H-dibenzo[a,d]cycloheptene The compound of Example 8 was dissolved in tetrahydrofuran and added to a suspension of lithium aluminum hydride in tetrahydrofuran and refluxed for 3 hrs. After washing with water, and extraction with ether, the subject compound was obtained; nmr (CDCl₃): τ 2.25–3.15 (m, 8H, arom), 5.21 (br d, 1H, J = 5Hz,

PhCHNH—), 5.90–6.90 (m, 5H, PhCH₂—, —OCH₂—, and —NH—), 7.25 (br t, 2H, —CH₂N(CH₃)₂), and 7.63 (s, 6H, —N(CH₃)₂).

Dosage Forms

The antidepressant agents of this invention can be administered as treatment for psychiatric depressions of the reactive and endogenous types by any means that produces contact of the active agent with the agent's site of action in the body of a mammal. In addition to their antidepressant activity they also have a beneficial sedative action. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice. The pharmaceutical composition consists essentially of a suitable pharmaceutical carrier and a compound of the present invention. "Consisting essentially of" is intended to have its customary meaning: namely, that all specified materials are very important in practicing the invention but that unspecified materials are not excluded so long as they do not prevent the benefits of the invention from being realized.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. The active ingredient can be administered orally at doses of about 0.01–100.0 mg./kg. or preferably at about 0.05–25.0 mg./kg. or more preferably at about 0.2–10 mg./kg. The active ingredient can also be given parenterally.

Dosage forms (compositions) suitable for internal administration contain from about 2 milligrams to about 10 milligrams of active ingredient per unit. In these pharmaceutical compositions the active ingredient will ordinarily be present in an amount of about 0.1–90% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

Capsules can be prepared by filling standard two-piece hard gelatin capsules with the following mixture using conventional encapsulating equipment:

| Active ingredient | 5 mg. |
|---|---|
| Lactose | 125 mg. |
| Talc | 12 mg. |
| Magnesium stearate | 3 mg. |

Capsules

A mixture of active drug in soy bean oil is prepared and injected by means of a positive displacement pump in gelatin to form soft gelatin capsules containing 5 mg. of the active ingredient. The capsules are washed in petroleum ether and dried.

Tablets

Tablets can be prepared by conventional procedures so that each unit will contain:

| Active ingredient | 5 mg. |
|---|---|
| Spray dried lactose | 150 mg. |
| Microcrystalline cellulose | 35 mg. |
| Magnesium stearate | 3 mg. |

Parenteral

Parenteral composition suitable for intra muscular administration is prepared so that each ml. contains:

| Active ingredient | 5 mg. |
|---|---|
| Sodium carboxy methyl cellulose | .75% |
| Polysorbate 80 | 0.04% |
| Benzyl alcohol | 0.9% |
| Sodium chloride | 0.9% |
| Water for injection Q.S. | 1 ml. |

Suspension

An aqueous suspension is prepared for oral administration so that each 5 mls. contain:

| Active ingredient | 5 mg. |
|---|---|
| Methylcellulose | 5% |
| Carboxy methyl cellulose | 5% |
| Syrup | 30% |
| Polysorbate 80 | 0.2% |
| Sodium saccharin | 2 mg. |
| Cherry flavor | 0.1% |
| Sodium benzoate | 5 mg. |
| Water Q.S. | 5 ml. |

Use

A standard procedure for detecting and comparing the antidepressant activity of compounds in this series for which there is good correlation with human efficacy is the prevention of tetrabenazine-induced sedation and depression in mice. (Everett, "The Dopa Response Potentiation Test and Its Use in Screening for Antidepressant Drugs", pp. 164–167 in "Antidepressant Drugs" [Proceedings of the First International Symposium], S. Garattini and M. N. G. Dukes, eds., 1967.).

Groups of 10 Carworth $CF_1S$ female mice, 18–21 g. each, were fasted 1.5 hours and were intubated with antagonist compounds at oral doses of 0, 5, 25, and 125 mg/kg or 0, 1, 3, 9, 27, and 81 mg/kg in 0.20 ml. of 1% Methocel (methylcellulose) 1.25% Tween 80. The mice were challenged 30 minutes later with tetrabenazine (as the methane-sulfonate), 32 mg/kg intraperitoneally (dissolved in 0.20 ml. 0.05M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5" × 8" with 0.33" mesh) either turned its head horizontally 30° in both direction or moved to the edge of the screen within 10 seconds after being placed on the screen. Relief from ptosis was recorded when exactly 2 seconds after placing the mouse facing the observer, lid closure was less than 50% in both eyes.

For comparison, the marketed antidepressant Amitriptyline was also tested, and an $ED_{50}$ (effective dose in 50% of the cases) was determined. The lower the $ED_{50}$, the better the antidepressant.

TABLE I

ANTAGONISM OF TETRABENAZINE-INDUCED DEPRESSION IN MICE ORALLY AT 1 HOUR POST-DRUG

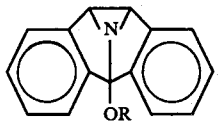

| R | $ED_{50}$ (mg/kg) | |
|---|---|---|
| | Exploratory | Ptosis |
| $CH_2CH_2NH_2$ | 2 | 1 |
| $CH_2CH_2NH_2$ . Maleate | 11.8 | 10.3 |
| $CH_2CH_2NH_2$ . Tartate | 3.3 | 2.7 |
| $CH_2CH_2N(CH_3)_2$ | 2 | 2 |
| $CH_2CH_2N(CH_3)_2$ . Maleate | 9 | 8 |
| $CH_2CH_2CH_2N(CH_3)_2$ | 67 | 56 |
| Amitriptylene . HCl | 3.7 | 1.5 |

Table II shows the antidepressant activity of 5,10-imino compounds of formula II.

TABLE II

ANTAGONISM OF TETRABENAZINE-INDUCED DEPRESSION IN MICE ORALLY AT 1 HOUR POST-DRUG BY

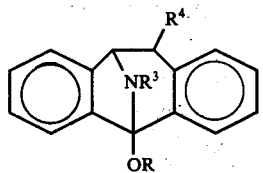

| R | $R^3$ | $R^4$ | $ED_{50}$ (mg/kg) | |
|---|---|---|---|---|
| | | | Exploratory | Ptosis |
| $CH_2CH_2N(CH_3)_2$ | H | Cl | 25 | 15 |
| $CH_2CH_2N(CH_3)_2$ | H | H | 15 | 15 |
| $CH_2CH_2NH_2$ | H | Cl | 37 | 37 |

Additionally, the compound of Table I were R = $-CH_2CH_2N(CH_3)_2$ was found not to potentiate tryptamine in mice which implies it is not a monoamine oxidase (MAO) inhibitor. An antidepressant which acts by inhibiting MAO is not acceptable. The test compound also potentiates hexabarbitol in mice, implying it has sedative qualities at high doses — a very desirable characteristic.

What is claimed is:

1. A compound of the formula

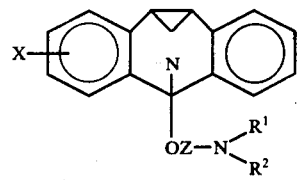

where
X is H, F, Cl, Br, $C_{1-4}$ alkyl, $C_{1-4}$ alkoxy, $CF_3$ or $C_{1-4}$ alkyl sulfonyl;
Z is $C_2$–$C_3$ alkylene; and
$R^1$ and $R^2$ independently are H, $C_{1-4}$ alkyl;
or its pharmaceutically suitable acid addition salt.

2. A compound of claim 1 where $R^1$ and $R^2$ independently are H or $CH_3$.

3. A compound of claim 1 wherein X is H, Z is ethylene, and $R^1$ and $R^2$ independently are H or $CH_3$.

4. The compound of claim 3 where $R^1$ and $R^2$ are H.

5. The compound of claim 3 where $R^1$ is H and $R^2$ is $CH_3$.

6. The compound of claim 3 where $R^1$ and $R^2$ are $CH_3$.

7. A pharmaceutical composition consisting essentially of a suitable pharmaceutical carrier and a compound of claim 1.

8. A pharmaceutical composition consisting essentially of a suitable pharmaceutical carrier and a compound of claim 2.

9. A pharmaceutical composition consisting essentially of a suitable pharmaceutical carrier and a compound of claim 3.

10. A pharmaceutical composition consisting essentially of a suitable pharmaceutical carrier and a compound of claim 4.

11. A pharmaceutical composition consisting essentially of a suitable pharmaceutical carrier and a compound of claim 5.

12. A pharmaceutical composition consisting essentially of a suitable pharmaceutical carrier and a compound of claim 6.

13. A method of alleviating depression in a mammal which comprises administering to the mammal as effective antidepressant amount of a compound of claim 1.

14. A method of alleviating depression in a mammal which comprises administering to the mammal an effective antidepressant amount of a compound of claim 2.

15. A method of alleviating depression in a mammal which comprises administering to the mammal an effective antidepressant amount of a compound of claim 3.

16. A method of alleviating depression in a mammal which comprises administering to the mammal an effective antidepressant amount of a compound of claim 4.

17. A method of alleviating depression in a mammal which comprises administering to the mammal an effective antidepressant amount of a compound of claim 5.

18. A method of alleviating depression in a mammal which comprises administering to the mammal an effective antidepressant amount of a compound of claim 6.

* * * * *